United States Patent
Brown et al.

(10) Patent No.: US 9,414,747 B2
(45) Date of Patent: Aug. 16, 2016

(54) FUNCTIONAL INTEGRATION OF VIRTUAL PROSTHESIS IN A TISSUE MODEL

(75) Inventors: Heather Anne Brown, Shelbyville, KY (US); Robert Royea, Redwood City, CA (US)

(73) Assignee: Qi Imaging, LLC, Redwood City, CA (US)

( * ) Notice: Subject to any disclaimer, the term of this patent is extended or adjusted under 35 U.S.C. 154(b) by 742 days.

(21) Appl. No.: 13/599,881

(22) Filed: Aug. 30, 2012

(65) Prior Publication Data

US 2013/0231911 A1    Sep. 5, 2013

Related U.S. Application Data

(60) Provisional application No. 61/529,109, filed on Aug. 30, 2011, provisional application No. 61/528,949, filed on Aug. 30, 2011, provisional application No. 61/528,984, filed on Aug. 30, 2011, provisional application No. 61/529,556, filed on Aug. 31, 2011, provisional application No. 61/529,610, filed on Aug. 31, 2011, provisional application No. 61/532,923, filed on Sep. 9, 2011, provisional application No. 61/532,944, filed on Sep. 9, 2011, provisional application No. 61/532,988, filed on Sep. 9, 2011, provisional application No. 61/543,644, filed on Oct. 5, 2011.

(51) Int. Cl.
| | | |
|---|---|---|
| *G06G 7/58* | (2006.01) | |
| *A61B 5/00* | (2006.01) | |
| *G06F 19/00* | (2011.01) | |
| *A61B 6/00* | (2006.01) | |
| *A61B 8/00* | (2006.01) | |
| *A61F 2/00* | (2006.01) | |
| *A61B 5/055* | (2006.01) | |
| *A61B 6/03* | (2006.01) | |
| *A61B 8/08* | (2006.01) | |
| *A61B 5/053* | (2006.01) | |

(52) U.S. Cl.
CPC ............... *A61B 5/004* (2013.01); *A61B 5/0035* (2013.01); *A61B 5/7425* (2013.01); *A61B 6/463* (2013.01); *A61B 8/463* (2013.01); *G06F 19/3437* (2013.01); *A61B 5/0044* (2013.01); *A61B 5/0059* (2013.01); *A61B 5/053* (2013.01); *A61B 5/055* (2013.01); *A61B 6/032* (2013.01); *A61B 6/037* (2013.01); *A61B 8/08* (2013.01); *A61F 2/00* (2013.01)

(58) Field of Classification Search
CPC ....................................................... A61F 2/00
USPC ............................................................. 703/11
See application file for complete search history.

(56) References Cited

U.S. PATENT DOCUMENTS

| | | | |
|---|---|---|---|
| 2006/0036253 A1* | 2/2006 | Leroux et al. | 606/73 |
| 2008/0063627 A1* | 3/2008 | Stucke et al. | 424/93.7 |
| 2010/0076563 A1* | 3/2010 | Otto et al. | 623/20.14 |
| 2011/0112808 A1* | 5/2011 | Anderson et al. | 703/2 |

* cited by examiner

*Primary Examiner* — Jerry Lin
(74) *Attorney, Agent, or Firm* — Fish & Tsang, LLP

(57) ABSTRACT

Systems and methods of integrating a virtual prosthesis with a tissue model are presented. Tissue characteristics and prosthesis characteristics can be leveraged to construct observable tissue models that present a model of mutual deformation, especially a time-varying mutual deformation, of a tissue and a possible prosthesis. The mutual deformation indicates how the tissue and prosthesis impact each other over time, possibly on a voxel-by-voxel basis based on deformable registration techniques.

20 Claims, 5 Drawing Sheets

FUNCTIONAL INTEGRATION OF VIRTUAL PROSTHESIS IN A TISSUE MODEL

This application claims priority to U.S. provisional applications having Ser. Nos.:

61/529,109, 61/528,949, and 61/528,984, filed Aug. 30, 2011;

61/529,556, and 61/529,610, filed Aug. 31, 2011;

61/532,923, 61/532,944, and 61/532,988 filed Sep. 9, 2011; and

61/54,3644 filed Oct. 5, 2011.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The field of the invention is tissue modeling technologies.

BACKGROUND

Prosthetic devices are available for many parts of the body, including orthopedics (e.g., knee or hip replacement), cardiovascular (e.g., cardiac valves, endovascular grafts) devices, neurological (e.g., deep brain stimulator, cochlear implant) devices, or other types of prosthetics. Medical imaging can be used for pre-operative planning to determine surgical approaches and appropriate sizing of the prosthesis. Unfortunately, known tissue imaging systems fail to provide tissue modeling information relating how a prosthetic device interacts with tissue in the model. Offering healthcare providers a path to observe, at least in a virtual model according to the disclosed techniques, how a prosthetic device interacts with a tissue would improve prosthetic device development and how a prosthesis and tissue mutually impact each other.

Thus there is still a need for providing method of modeling prosthesis and tissues.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

SUMMARY OF THE INVENTION

The inventive subject matter provides apparatus, systems and methods that allow individuals to observe prosthetic device—tissue interactions. One aspect of the inventive subject matter includes methods of creating virtual tissue models. Healthcare providers, or other authorized user, can access a tissue modeling engine. The tissue modeling engine electronically receives prosthetic characteristics (e.g., size, dimension, mechanical properties, electrical properties, etc.) and folds the characteristics into a virtual model of the prosthesis. Further, the engine receives tissue characteristics of one or more target tissues that would likely be in contact with the prosthesis. The modeling engine constructs an observable model that combines a tissue model and a prosthesis model. The modeling engine then presents the observable model (e.g., 2D, 3D, 4D or other dimensional rending), which illustrates a time varying mutual deformation between the prosthesis and tissue.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
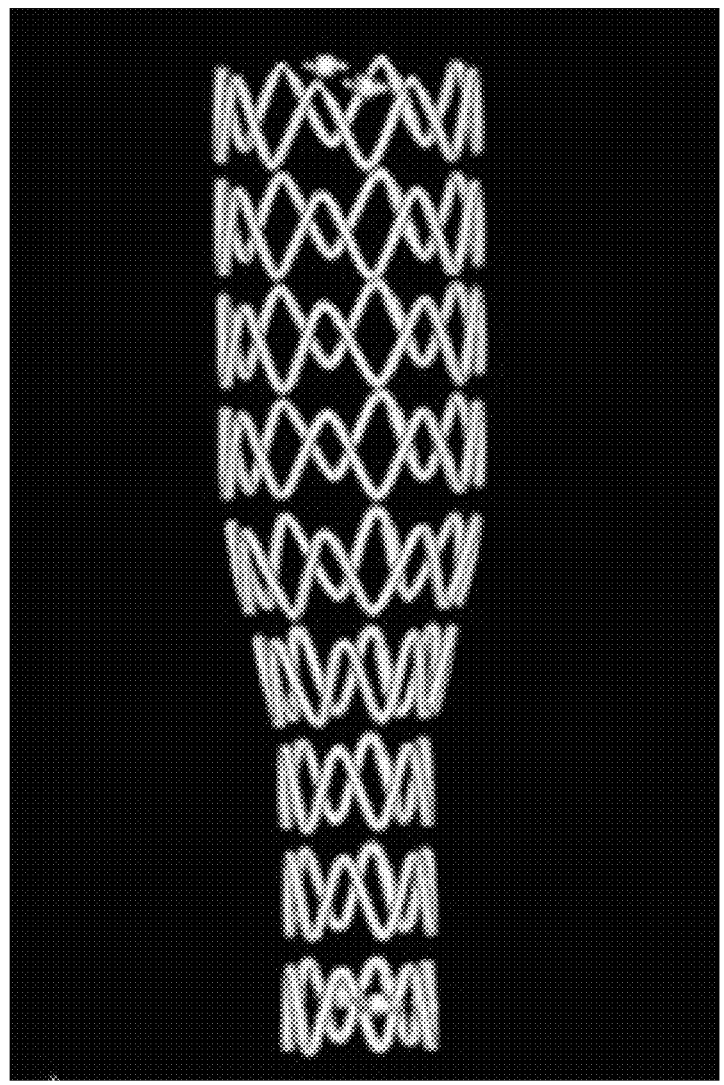
FIG. 1 is an example of a model prosthesis as an synthetic aortic graft.

It should be noted that while the following description is drawn to a computer/server based tissue analysis or modeling systems, various alternative configurations are also deemed suitable and may employ various computing devices including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges preferably are conducted over a packet-switched network, the Internet, LAN, WAN, VPN, or other type of packet switched network.

One should appreciate that the disclosed techniques provide many advantageous technical effects including tissue modeling engines capable of generating signals that configure one or more output devices to produce an observable model that illustrates a time varying mutual deformation between a virtual prosthesis and a modeled tissue.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously. Further, the terms "coupled to" and "coupled with" are also used euphemistically to represent "communicatively coupled with" within a networking context, where two or more devices are able to exchange data over network possibly through one or more intermediary devices.

Qi Imaging (formally ZioSoft, Inc.) has pioneered systems and methods for deformable registration as described in the following issued patents and published patent applications. The disclosed techniques build upon these foundational works:

U.S. Pat. Nos. 7,310,095; 7,420,575; 7,424,140; 7,502,025; 7,529,396; 7,574,027; 7,576,741; 7,616,205; 7,620,224; 7,623,695; 7,639,855; 7,639,867; 7,647,593; 7,653,231; 7,689,018; 7,706,588; 7,738,701; 7,778,451; 7,782,507; 7,796,835; 7,817,877; 7,825,924; 7,853,057; 7,860,284; 7,860,949; 7,869,638; 7,873,197; 7,907,763 and

U.S. 2006/0155800; U.S. 2007/0223832; U.S. 2008/0075346; U.S. 2008/0101672; U.S. 2008/0136815; U.S. 2008/0170768; U.S. 2008/0297509; U.S. 2009/0003668; U.S. 2009/0019400; U.S. 2009/0119609; U.S. 2009/0129642; U.S. 2009/0174729; U.S. 2009/0290769; U.S. 2010/0007663; U.S. 2010/0142788; U.S. 2011/0075888; U.S. 2011/0075896; WO 2011/037853; WO 2011/037860.

The following discussion relates to construction of an observable model that illustrates possible interactions between a prosthesis and a tissue with which the prostheses is coupled. As an example, consider Endovascular Aortic Repair (EVAR) of aneurysms. EVAR is a common procedure that uses a synthetic graft (i.e., a prosthesis) to stabilize aortic aneurysms. The key to a successful repair is correct sizing and placement of the graft. The pre-operative assessment is based on a single phase or multi-phase CT scan. Historically, the size of the graft is selected by measuring distances along the centerline and diameters of numerous cross sections (2D) through the aorta and other involved vessels. Each manufacturer offers standard sizes of varying configurations of the diameter and lengths. A volumetric model of the graft itself can be obtained by scanning the graft; for example, a CT scan of the graft clearly shows the metal 'skeleton' of the graft as illustrated in FIG. 1. Complications can arise from too much tortuousity in the vessel, misplaced grafts relative to the aneurysm, or other vessel branches.

Figure 2:
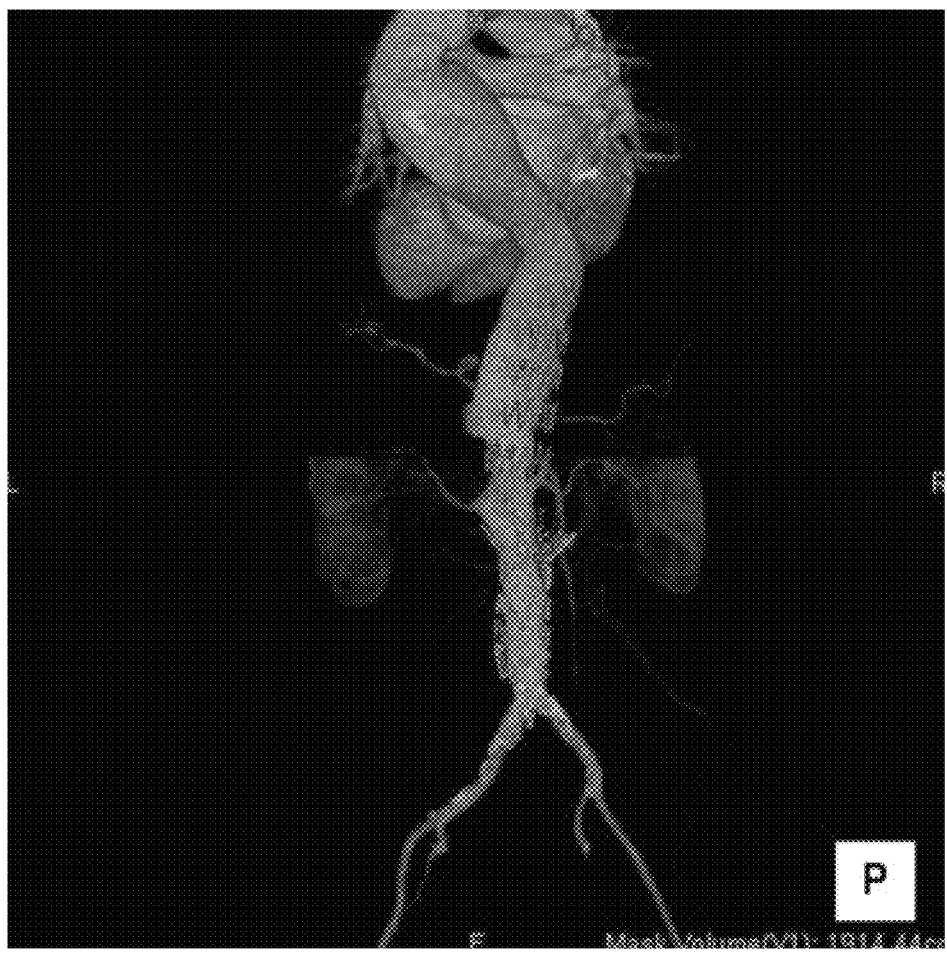
FIG. 2 is an example of an observable model that includes a tissue model and a virtual prosthesis model.
Figure 3:
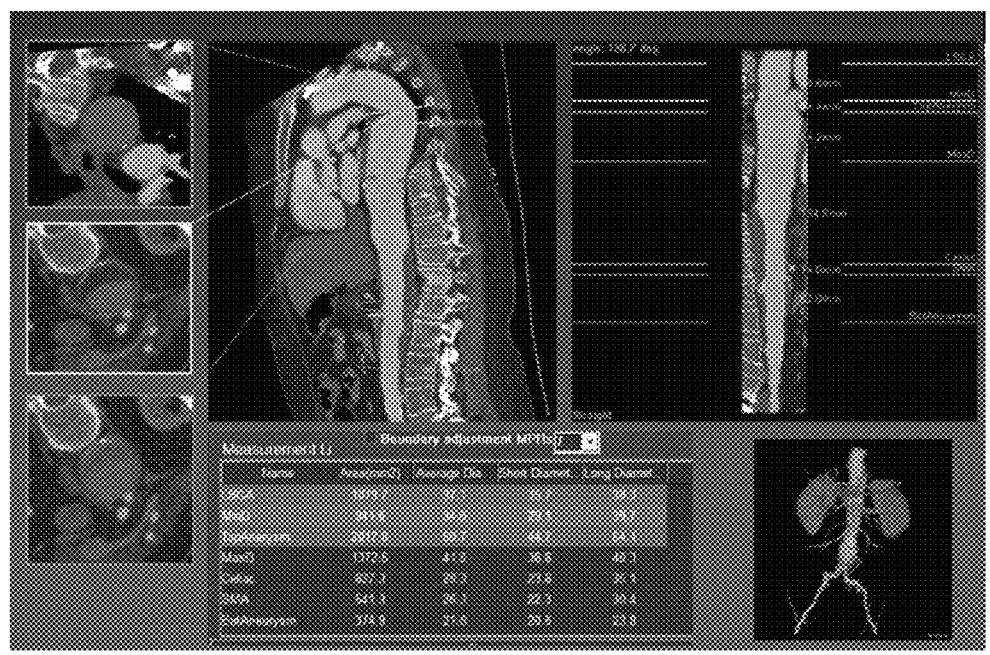
FIG. 3 is an example interface allowing a user to measure physical points of a tissue model and adjust a virtual prosthesis model.

The disclosed inventive subject matter leverages deformable registration techniques to allow a healthcare provide to more accurately determine proper characteristics of a prosthesis (e.g., the graft). The healthcare provider can choose from any of the available grafts to fuse with the patient's data to determine the best sizing as illustrated in FIG. 2. Deformable registration uses a centerline as initial registration and then can use deformation to align the graft to the patent lumen of a vessel. Automated measurements, possibly real-time measurements, can be provided within a tissue-prosthesis model based on various possible placements of the virtual grafts as shown in FIG. 3.

Although the previous introductory example and following discussion focuses on EVAR, one should appreciate that the disclosed modeling systems allow for modeling a prosthesis to other types of tissues, anatomical structures, or other body parts as discussed below. The disclosed modeling systems provide insight into how prosthesis could or would behave when coupled with the target tissue well before the prosthesis is implanted or attached. Modeling systems can also provide insight into how the prosthesis could interact neighboring tissues.

Figure 4:
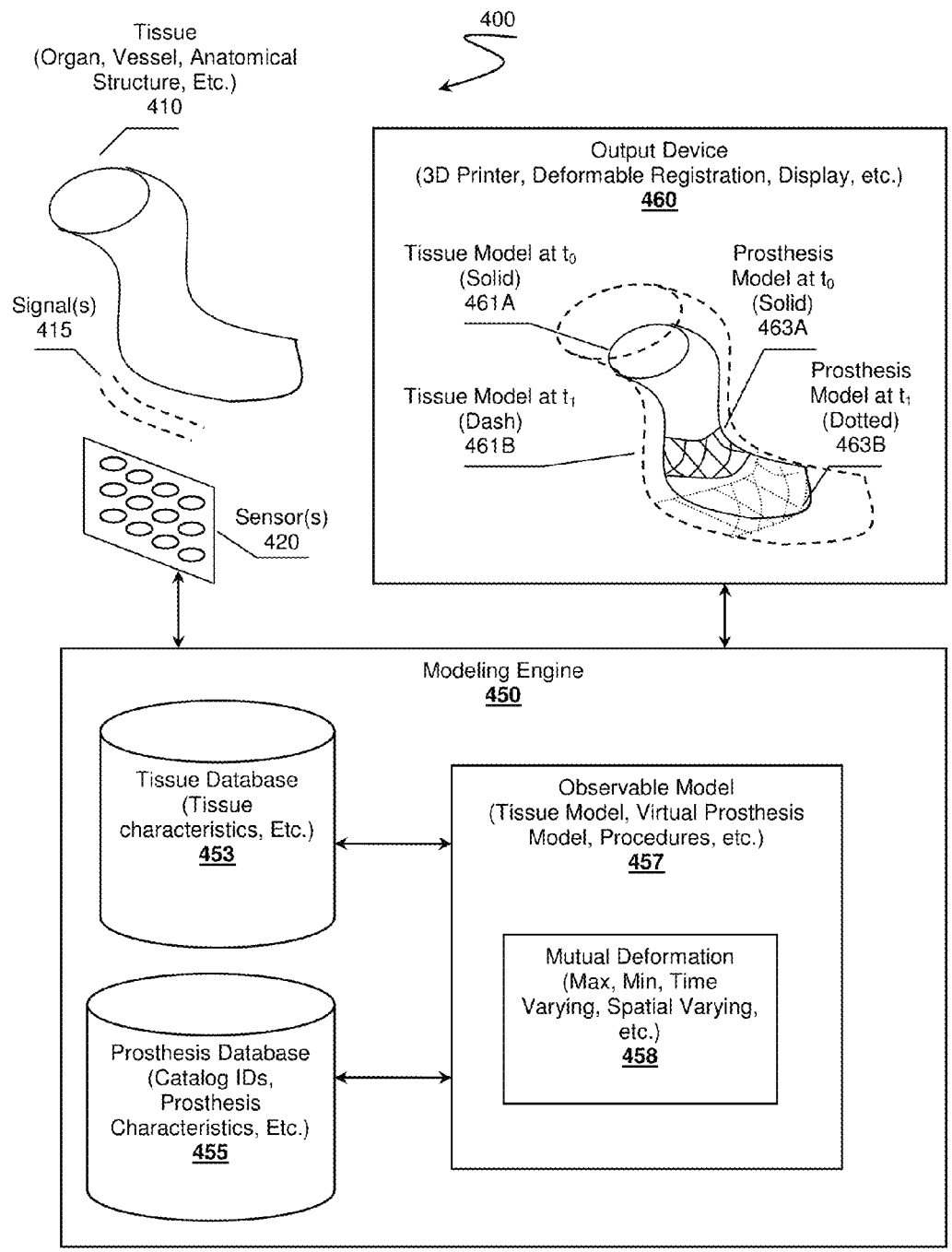
FIG. 4 is a schematic of a tissue and prosthetic modeling ecosystem.

FIG. 4 illustrates tissue modeling and analysis system 400 where information related to prostheses and tissue 410 can be combined to construct observable model 457. Observable model 457 represents a model of a virtual prosthesis along with a model of tissue 410 in a manner that allows users to observe how a prosthesis could or might interact with tissue 410 over time. For example, observable model 457 can include mutual deformation 458 indicating how the virtual prosthesis and the model of tissue 410 deform with respect to each other from time $t_0$ to $t_1$ as illustrated. Although observable model 457 illustrates how a prosthesis interacts with a target tissue to which the prosthesis is coupled, one should appreciate that tissue 410 could also include a neighboring tissue. For example, tissue 410 could include a bone to which an artificial joint couples. In such a scenario, tissue 410 could also include neighboring muscles, cartilage, ligaments, or other portions of the body.

Tissue 410 can include a wide variety of tissues, preferably including tissues that are amenable to couple with a prosthesis. Example tissues include vessels, bone, arteries, valves, joints, organs, anatomical structures, or other types of tissues. Further, tissue 410 can include tissues from various types of patients: human, mammals, or other animals. The example in FIG. 1 illustrates tissue 410 as a tubular structure, possibly an aorta. However, the reader should appreciate that tissue 410 can comprise other structures or tissue (e.g., bone, organs, muscle, etc.).

In some embodiments, modeling system 400 can obtain tissue characteristics from signals 415 originating from tissue 410 where signals 415 include information reflecting one or more tissue properties possibly depending on the modality of signals 415. For example, in embodiments where signals 415 include acoustic signals (e.g., ultrasound), signals 415 can be representative of size, shape, volume, or density of tissue 415. In other embodiments, signals 415 could include electromagnetic signals (e.g., MRI, X-Rays, CT, etc.) that could represent electrical properties of tissue 410 (e.g., conductivity, inductivity, resistivity, etc.).

Regardless of the form signals 415, signals 415 can be received or otherwise obtained via one or more sensors 420, which can be configured to convert signals 415 into observable data using known techniques. For example, when signals 415 include acoustic signals, sensors 420 could include ultrasound transducers, which collect and convert signals 415 into digital data. The digital data can then be further processed to give rise to tissue characteristics via an analysis engine or even by modeling engine 450.

In the example shown, tissue characteristics can be stored in tissue database 453, which is configured to store information related to tissue 410 or other tissues, possibly including neighboring tissues. Tissue database 453 can store tissue characteristics according to one or more schemas that can be leveraged by modeling engine 450. Further, the tissue characteristics can cover a broad spectrum of properties. Example tissue properties include electrical properties (e.g., resistance, conductivity, inductance, etc.), chemical properties (e.g., p.H.,), biological properties (e.g., innervation, muscle type, vascularity, etc.), mechanical properties (e.g., stress, strain, shear, elasticity, hardness, density, etc.), tissue state (e.g., necrotic, living, etc.), geometric properties (e.g., lengths, widths, size, volume, dimensions, etc.), temporal properties (e.g., movement with time, state changes, etc.), or other types of tissue properties.

Although modeling system 400 illustrates obtaining, directly or indirectly, tissue characteristics of tissue 410, possibly in real-time, one should appreciate that tissue database 453 can include a priori known tissue properties. The a priori known tissue properties can include information obtained over a population of patients. For example, the a priori tissue properties can include general size, shape, dimensions; known temporal movements or changes; statistical properties (e.g., average properties) across populations of patients, or other known information. Consider a tissue 410 as an aorta. Tissue database 453 can include statistical properties representing how, on average across a population of patients, a typical aorta's elasticity changes with age. Such a priori information is considered advantageous when constructing observable model 457 that depicts how tissue 410 and a prosthesis interact over portions of a lifetime of a patient.

Modeling engine 450 preferably also has access to one or more prosthesis characteristics. One should appreciate that although physical properties are considered important for properly constructing a virtual prosthesis within observable model 457, prosthesis characteristics can also include a wide spectrum of possible properties. In more preferred embodiments, the prosthesis characteristics are complementary to the tissue characteristics. Example prosthesis characteristics can include electrical properties (e.g., resistance, conductivity, inductance, etc.), chemical properties (e.g., p.H., etc.), mechanical properties (e.g., stress, strain, shear, elasticity, hardness, density, etc.), state, geometric properties (e.g., lengths, widths, size, volume, dimensions, etc.), temporal properties (e.g., degradation, ability to move or flex with time, state changes, wear or tear, etc.), or other prosthesis properties.

As illustrated, prosthesis characteristics can be stored in prosthesis database 455, which is configured to store properties. In some embodiments, prosthesis database 455 can comprise a catalog of known prosthesis, possibly stored according to a schema that indexes the prosthesis by type, make, model, manufacturer, size, dimension, target tissue type, product code, or other schema.

Although prosthesis database 455 can include known prosthesis information, prosthesis database 455 can be populated with information obtained from tissue 410. Such an approach is considered advantageous when constructing a desirable or custom prosthesis that specifically targets tissue 410. For example, through observation of tissue 410 preferably through deformable registration imaging system, modeling engine 450 can determine acceptable properties of a prosthesis (e.g., material or materials, size, shape, dimension, structure, hardness, elasticity, etc.). Modeling engine 450 can then obtain a prosthesis template from prosthesis database 455 possibly from a manufacturer, and then flesh out the attributes of the template based on the determined properties. The fleshed out template can then be submitted to the manufacturer, where the manufacturer could be a remote facility or even a local manufacturing facility (e.g., a 3D printer). Example prostheses include a stent, a valve, a joint replacement, a sensory implant (e.g., ocular, cochlear, vestibular, hearing aid, cornea, etc.), an electrical implant (e.g., pacemaker, neural shunt, etc.), a living tissue (e.g., transplant, graft, etc.), an artificial muscle, or other types of prostheses known or yet to be invented.

Modeling engine 450 receives or otherwise obtains prosthesis characteristics or tissue characteristics, possibly from prosthesis database 455 and tissue database 453 respectively. In some embodiments, a user can select one or more of prosthesis from prosthesis database 455 where prosthesis database 455 is configured to store available prosthesis as discussed previously.

Once modeling engine 450 has access to the various characteristics, modeling engine 450 constructs observable model 457 comprising a prosthesis model (i.e., prosthesis models 463A and 463B; collectively referred to as prosthesis model 463) as a virtual prosthesis according to the characteristics of the prosthesis and a tissue model (i.e., tissue models 461A and 461B; collectively referred to as tissue model 461) according to the obtained characteristics. Observable model 450 can be constructed through known techniques including those used in ultrasound, MRI systems, CT scan systems, X-Ray systems, or other systems. More preferred embodiments leverage a deformable registration imaging system that operates as modeling engine 450. For example, the deformable registration imaging systems offered by Qi Imaging can be suitably adapted for use with the disclosed techniques. The deformable registration imaging system conducts finite analysis of tissue 415 via tissue characteristics and constructs a virtual prosthesis based on the prosthesis characteristics to construct or present observable model 457 (see FIGS. 2 and 3).

Observable model 457 preferably includes mutual deformation 458 indicating how a tissue model 461 and prosthesis model 463 affect each other due to difference in their respective properties. Mutual deformation 458 preferably includes a time varying mutual deformation that provides insight into how tissue model 461 and prosthesis model 463 change with time due to their respective influence on the other. Still, other forms of mutual deformation 458 are also considered to fall within the scope of the inventive subject matter possibly including spatial mutual deformations, or effects generated due to differences of other complementary properties. For example, differences in electrical properties (e.g., conductivity, resistance, ionization, etc.) between the prosthesis and tissue 410 or other neighboring tissues could also be included in a presentation of mutual deformation 458.

In the example shown, mutual deformation 458 is presented through modeling engine 450 by configuring output device 460 to present observable model 457, which includes a depiction of a time varying mutual deformation between the prosthesis model 463 and the tissue model 461. The time varying mutual deformation is illustrated by presenting a snap shot of tissue model 461A and prosthesis model 463A at an initial time $t_0$ and a superimposed snap shot of tissue model 461B and prosthesis model 463B at a later time $t_1$. One should appreciate the value of the presented example. Tissue model 461 can be based on actual measured values of tissue 410 possibly representing how dimensions, strain, or other properties of an aorta change with time through a cardiac cycle, while prosthetic model 463 indicates the behavior a virtual prosthesis during such a cycle. Still further, one should appreciate that effects of the virtual prosthetic feedback into the tissue model 461 in a manner that tissue module 461 does not necessarily represent a pure observed module, but can include a hybrid of an actual observed tissue 410 behavior over time along with the impact from a proposed prosthesis. For example, a stiffness or hardness of a graft could restrict movement or expansion of tissue 410. The inventive subject matter is considered to include incorporating second, tertiary, or other higher order impacts within mutual deformation 458. To continue the previous example, a graph that is too restrictive might, over a long term, impact a patient's blood pressure or hormone balance.

Although mutual deformation 458 is presented as an example of changes in physical properties over time via output device 460, mutual deformation 458 can included a much broader range of possible deformations that can arise based on difference in properties between tissue model 461 and prosthesis model 463. Other example differences that can give rise to mutual deformation 458 include chemical changes (e.g., pH), electrical changes (e.g., conductivity, inductance, resistance, etc.), physical changes (e.g., size, dimension, strain, stress, etc.), biological changes (e.g., apoptosis, etc.) if the prosthetic comprises living tissue, or other changes that can be modeled based on the input properties of the prosthetic and tissue. Thus, output device 460 can be configured, via modeling engine 450, to highlight or indicate the deformations. For example mutual deformation 458 can include physical elasticity information, chemical changes, or other changes that arise to mutual behaviors.

In view that modeling engine 450 can construct observable model 457 using finite analysis, preferably on a voxel-by-voxel basis, mutual deformation 458 can be presented on a voxel-by-voxel basis. Mutual deformation 458 can therefore indicate mutual behavior with respect to surface affects as well as volume effects down to a voxel. Consider a scenario where chemical properties (e.g., conductivity, resistance, etc.) are of a concern possibly for a bone implant. Mutual deformation 458 can include an indication of how the implant's electrical properties can impact the bone over extended periods of time. Such an approach is advantageous for scenarios where the prosthesis will remain in place for over significant portions of a patient's lifetime. Further, mutual deformation 458 can be based on modeled activities, such as sporting events to indicate how the bone and implant would behave under mechanical stress. Such an approach is useful for addressing sports injuries.

Output device 460 presents mutual deformation 458 as two snap shots in time on a signal image. Observable model 457 can be used to configure output device 460 to present other formats. Example formats can include a series of snap shots next to each other, an apparently continuous video sequence (e.g., real-time, substantially real-time; over seconds, minutes, days, weeks, months, years, etc.), animations, as simulation of real-world conditions, or other formats. For example, observable model 457 can include a depiction of mutual deformation 458 during a percutaneous procedure. Further, deformations can be presented in different formats including false color images, contours, highlights, alerts, notifications, alarms, gauges, or other formats (see FIG. 3 for examples). Especially preferred embodiments include observable models 457 that indicate incompatibilities between tissue model 461 and prosthesis model 463 based on their respective properties where an incompatibility could be identified based on trigger criteria defined in terms of differences in tissue and prosthetic properties, especially as a function of time.

Output device 460 preferably includes one or more computing devices capable of rendering the mutual deformation 458 in a desired manner. As illustrated, output device 460 represents a component of a deformable registration system. However, output device 460 can include other types of devices including 3D printers capable of "printing" a real prosthesis or modeled prosthesis with color highlights showing strain or stress points, cell phones, tablets, computer controlled milling machines, or other types of output devices.

An astute reader will readily appreciate the value of presenting mutual deformation 458 and possible incompatibilities. For example, a finite element analysis of a graft skeleton model can be performed to estimate a probability of failure based on the amount of predicted deformation (e.g., sheer, strain, compression, tension, torsion, etc.). Thus mutual deformation 458 can include predicted deformation that can be based on an absolute deformation of the tissue or prosthesis device, or a relative deformation between the tissue and prosthesis, possibly during a simulation of a specific activity. Again, the reader is reminded that a simulation could include a hybrid simulation that incorporates real raw tissue data obtained during the activity and integrating a virtual prosthesis into the model so that the simulated mutual impact of the tissue and prosthesis can be observed.

Additionally, the current standard for sizing and placement of hip prosthetics is based off of 2D measurements from raw data. As described above, the prosthesis themselves can be scanned into the system or imported as a 3D model and registered to the patient's anatomy. Using the registration (i.e., rigid or deformable), finite element analysis can be performed on the fused system to provide more realistic boundary conditions or other prosthetic-tissue interactions.

Figure 5:
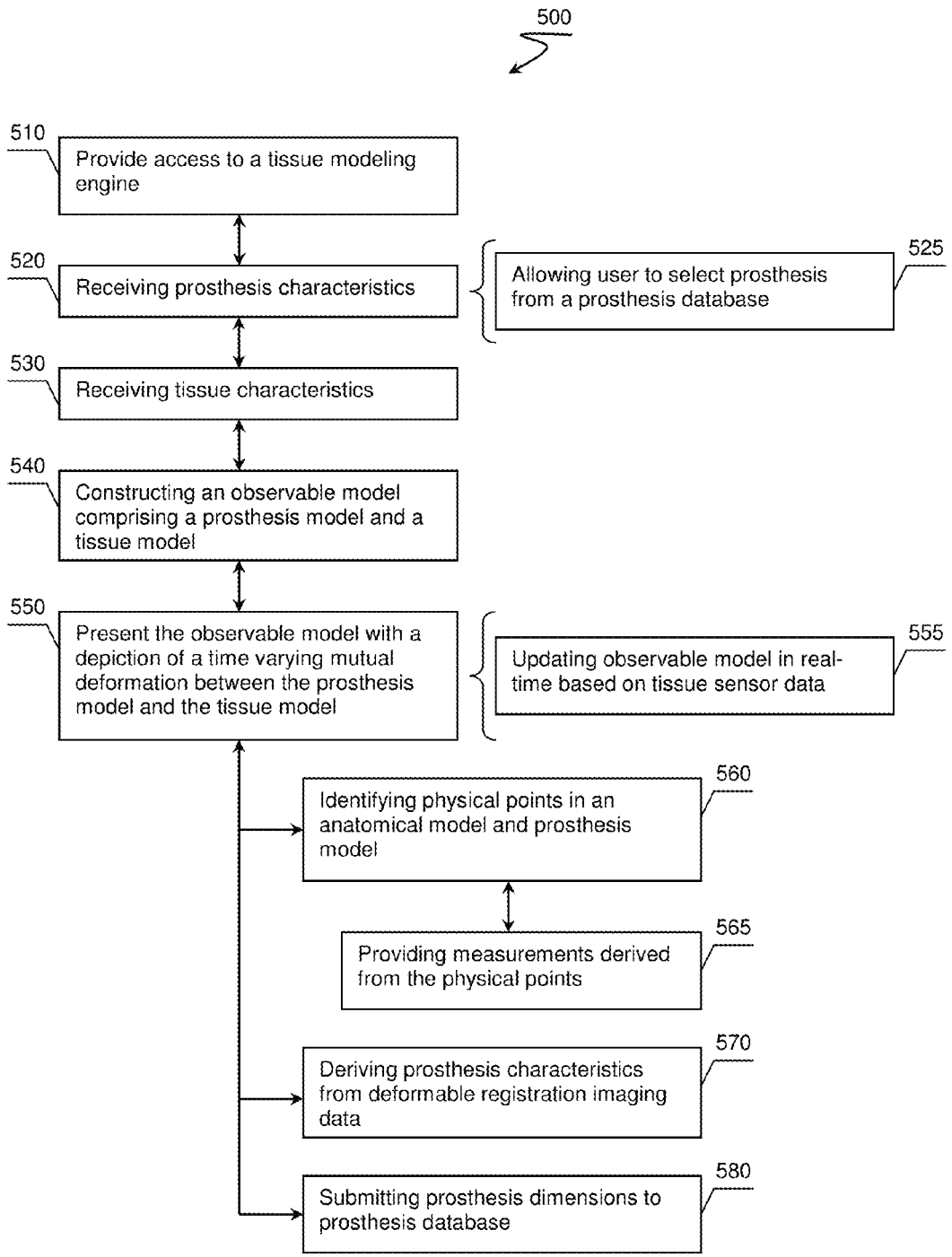
FIG. 5 is a schematic of a method of functional integration of a virtual prosthesis in a tissue model.

FIG. 5 presents method 500 of function integration of a virtual prosthesis with in a tissue model. Step 510 includes providing access to a tissue modeling engine. Providing access to the engine can comprise configuring a computing device or processor (e.g., single core, multi-core, etc.) to execute software instructions, allowing or authorizing access to a modeling engine via a cloud implementation (e.g., platform as a service, infrastructure as a service, software as a service, etc.), or other techniques that allow users to gain access to the functionality of the disclosed techniques that employ the inventive subject matter. In especially preferred embodiments, access is provided in exchange for a fee; a subscription, a signal payment, an hourly rate, a per-use charge, or other type of charges.

Step 520 includes the modeling engine receiving or otherwise obtaining prosthesis characteristics that represent parameters for constructing a virtual prosthesis within an observable tissue model. In some embodiments, the prosthesis characteristics can be obtained from a prosthesis database storing known prosthesis products as suggested by step 525. For example, a healthcare provider can select a desired prosthesis from the prosthesis database for inclusion into the model, where the selected prosthesis from the database can have the desirable characteristics. Such characteristics can be obtained from the manufacturer or possibly via datasheets.

Step 530 can comprise the modeling engine receiving or otherwise obtaining tissue characteristics. Such tissue characteristics can be obtained directly or indirectly from a target tissue, possibly via one or more sensor systems (e.g., ultrasound, MRI, fMRI, CT, PET, etc.). In additional embodiments the tissue characteristics can be obtained based on previously measured or a priori known information, possibly derived across a population of patients. Such tissue characteristics can be classified according a number of patient categorizations including race, gender, genetic markers, disease, cancer, age, geography, or other demographics. Further the tissue characteristics can include statistical information including averages, modes, distribution widths, means, probability or frequency distribution information, or other information.

Step 540 preferably comprises the modeling engine constructing an observable model comprising a prosthesis model according to the characteristics of the prosthesis and a tissue model according to the characteristics of the tissue. The observable model can be derived according to known techniques, included those developed and deployed using finite analysis, on a voxel-by-voxel basis, as pioneered by Qi Imaging.

Step 550 includes the modeling engine configuring an output device (e.g., computer, deformable registration imaging system, 3D printer, etc.) to present the observable model, which preferably includes a time varying mutual deformation between the prosthesis model and the tissue model. The mutual deformation can include an animation, false color highlights, stack charts, linear graphs, or other formats that indicate the mutual deformation. Further, the mutual deformation indicates a mutual impact beyond physical deformation with respect to physical properties, but can also include mutual impact based on electrical properties, mechanical properties, biological properties, chemical properties, or other types of properties.

In view that tissue characteristics can be obtained in substantially real-time, method 500 can include step 555, which includes updating the observable model on the output device in substantially real-time based on acquired tissue sensor data. For example, captured ultrasound data of cardiac tissue can be combined with the virtual prosthesis to construct a simulated real-time model of how the virtual prosthesis and cardiac tissue might behave together. Such an approach is advantageous because it does not require invasive procedures to determine the nature of a possible prosthesis.

Contemplated methods can further include additional steps. For example, step 560 can include allowing one or more user to identify one or more physical points in space, or time, based on the presented observable model (e.g., an image) of an anatomical structure. The modeling engine can then generate one or more measurements at step 565 associated with the identified points. Consider the example illustrated in FIG. 3. The illustrated interface allows identification and selection of points in space, and time, to determine an appropriate size for a graft. The measurements can represent information beyond physical dimensions (e.g., distance, length, widths, area, volume, etc.). Example additional measurements can include stress, strain, density, conductivity, perfusion, or other measurements of the tissue or prosthesis properties. Such approaches are considered useful especially when determining how cardiac valve area or mechanical properties behave over time.

In some embodiments, the modeling engine allows a user to select available prosthesis, providing prosthetic dimensions to an external prosthetic database (e.g., EMR, etc.), or input physical points in the model from which the modeling engine derives measurements (e.g., a distance, an area, a volume, a stress, a strain, a perfusion, etc.) relating to the tissue or prosthetic.

Step 570 can further include obtaining prosthesis measurements from the observable model and submitting the measurement to a prosthesis database. Preferably, the measurements are derived from a deformable registration imaging system (see FIG. 3). For example, while observing a tissue model, a technician can determine the appropriate measurements for the target prosthesis (e.g., stent, valve, pacemaker, etc.), especially with respect to how the measurement behave with time.

At step 580, the measurements; dimensions, material, or mechanical properties for example, can then be submitted to a prosthesis database possibly accessible by a manufacturer. The manufacturer can then construct the prosthesis according to measurements, especially measurements that take into account time varying deformation.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method, comprising:
   providing access to a tissue modeling engine;
   receiving, by the modeling engine, prosthesis characteristics of a prosthesis and tissue characteristics of a tissue;
   constructing, by the modeling engine, an observable model comprising a prosthesis model according to the characteristics of the prosthesis and a tissue model according to the characteristics of the tissue that includes a time varying mutual deformation indicating how the prosthesis model and the tissue model deform one another over time; and
   configuring a display to present the observable model including a depiction of the time varying mutual deformation between the prosthesis model and the tissue model, wherein the depiction comprises at least two snap shots of a deformation of the prosthesis model and a deformation of the tissue model.

2. The method of claim 1, wherein the mutual deformation comprises a physically elastic change.

3. The method of claim 1, wherein the mutual deformation comprises a chemical change.

4. The method of claim 1, wherein the display presents the depiction of the time varying mutual deformation as an apparently continuous video sequence.

5. The method of claim 1, further comprising allowing the user to select the prosthesis from a prosthesis database of available prosthesis, each having respective prosthesis characteristics.

6. The method of claim 1, further comprising identifying multiple physical points identified on an image of at least one of an anatomical tissue model of the tissue and the prosthetic model of the prosthesis within the observable model and providing a measurement derived from the physical points.

7. The method of claim 6, wherein the measurement comprises at least one of the following: a distance, an area, a volume, a stress, a strain, and a perfusion.

8. The method of claim 1, wherein the step of configuring the display to present the observable model including a depiction of the time varying mutual deformation between the prosthesis model and the tissue model comprises presenting a snap shot of the tissue model and the prosthesis model at an initial time and a superimposed snap shot of the tissue model and the prosthesis model at a later time.

9. The method of claim 1, wherein the mutual deformation incorporates at least a tertiary order impact.

10. A method, comprising:
    providing access to a tissue modeling engine;
    receiving, by the modeling engine, prosthesis characteristics of a prosthesis and tissue characteristics of a tissue;
    constructing, by the modeling engine, an observable model comprising a prosthesis model according to the characteristics of the prosthesis and a tissue model according to the characteristics of the tissue that includes a mutual deformation indicating how the prosthesis model and the tissue model deform one another over time; and
    configuring a 3D printer to print the observable model including the mutual deformation as a modeled prosthesis having highlights showing stress points from the mutual deformation.

11. The method of claim 10, wherein the modeled prosthesis comprises at least one of a stent, a valve, a joint, a sensory implant, an electrical implant, a living tissue, a transplant, and an artificial muscle.

12. The method of claim 10, further comprising deriving at least one of the characteristics of the modeled prosthesis from deformable registration imaging data of the tissue.

13. The method of claim 10, wherein the mutual deformation comprises an electrical change.

14. The method of claim 13, wherein the electrical change comprises an indication of how the prosthesis' electrical properties can impact a bone over time.

15. The method of claim 10, wherein the 3D printer is further configured to highlight the mutual deformation on the modeled prosthesis.

16. The method of claim 15, wherein the highlights are colored highlights that show strain points.

17. The method of claim 15, wherein the highlights are colored highlights that show stress points.

18. The method of claim 10, wherein the mutual deformation comprises a physically elastic change.

19. The method of claim 10, further comprising allowing the user to select the prosthesis from a prosthesis database of available prosthesis, each having respective prosthesis characteristics.

20. The method of claim 10, wherein the mutual deformation incorporates at least a tertiary order impact.

\* \* \* \* \*